(12) United States Patent
Devine et al.

(10) Patent No.: US 7,429,674 B2
(45) Date of Patent: Sep. 30, 2008

(54) PROCESS FOR PREPARING FLUOROLEUCINE ALKYL ESTERS

(75) Inventors: Paul Devine, Tinton Falls, NJ (US); John Limanto, Rahway, NJ (US); Ali Shafiee, Westfield, NJ (US); Veena Upadhyay, Westfield, NJ (US)

(73) Assignee: Merck & Co. Inc.., Rahway, NJ (US)

( * ) Notice: Subject to any disclaimer, the term of this patent is extended or adjusted under 35 U.S.C. 154(b) by 491 days.

(21) Appl. No.: 11/106,214

(22) Filed: Apr. 14, 2005

(65) Prior Publication Data

US 2005/0234128 A1  Oct. 20, 2005

(51) Int. Cl.
*C07C 229/00* (2006.01)
*C07C 205/00* (2006.01)

(52) U.S. Cl. .......................... 560/155; 562/553; 560/172

(58) Field of Classification Search ................. 514/561; 562/553, 172; 560/155, 172
See application file for complete search history.

(56) References Cited

FOREIGN PATENT DOCUMENTS

WO    WO 03/075836    9/2003

*Primary Examiner*—Taylor Victor Oh
(74) *Attorney, Agent, or Firm*—Nicole M. Beeler; David A. Muthard

(57) ABSTRACT

This invention relates to a stereoselective preparation of fluoroleucine alkyl esters.

10 Claims, No Drawings

PROCESS FOR PREPARING FLUOROLEUCINE ALKYL ESTERS

BACKGROUND OF THE INVENTION

Fluorinated amino acids and their derived peptides have been widely employed as potential pharmaceutical agents due to their broad biological properties, which include enzyme inhibitors, receptor antagonist and lipophilicity enhancing agents. While much development has focused on preparation of various fluorinated analogues of natural and non-proteinogenic amino acids, asymmetric synthesis of γ-fluoro-α-amino acids still remains a challenge. In this regard, stereoselective incorporations of the γ-F-containing side chain have been mostly executed by either a chiral auxiliary-directed diastereoselective alkylation or a chiral phase transfer-catalyzed alkylation of protected amino acid precursors.

The instant invention describes a novel stereoselective preparation of fluoroleucine alkyl esters which comprises an efficient throughput process.

SUMMARY OF THE INVENTION

By this invention, there is provided a process for the preparation of a compound of structural formula I:

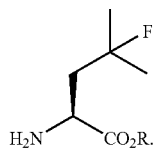

I wherein R is hydrogen or $C_{1-6}$ alkyl;

comprising the steps of:
a. Alkylating an imine of formula II. with a fluorotriflate electrophile to form a substititued imine;

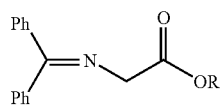

II.

b. Forming an azlactone;
c. Enzymatically opening the azlactone to form an alkyl amide;
d. Deprotecting the alkyl amide with an oxidizing agent to produce the compound of formula I.

DETAILED DESCRIPTION OF THE INVENTION

By this invention, there is provided a process for the preparation of a compound of structural formula I:

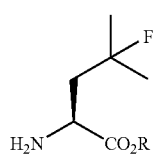

I wherein R is hydrogen or $C_{1-6}$ alkyl; comprising the steps of: alkylating an imine with a fluorotriflate electrophile to form a substititued imine; forming an azlactone; enzymatically opening the azlactone to form an alkyl amide; and deprotecting the alkyl amide with an oxidizing agent.

The alkylation of the imine takes place in the presence of a strong base. In one aspect of the invention, the strong base has a pKa of greater than 20. In one class of the invention, the strong base is potassium t-butoxide, lithium t-butoxide, sodium t-butoxide, LDA, sodium hydride, n-BuLi, sec-BuLi, t-BuLi, LiHMDS, NaHMDS, KHMDS or LiTMP. In a subclass of the invention, the strong base is potassium t-butoxide.

The azlactone formation is performed with a carbonyl activator. In one class of the invention, the carbonyl activator is EDC, DCC, Acetic anhydride ($Ac_2O$), pivaloyl chloride, or 1-cyclohexyl-3-(2-morpholinoethyl)carbodiimide metho-p-toluenesulfonate (CMC metho-p-toluenefulfonate). In a subclass of the invention, the carbonyl activator is EDC.

The enzymatic ring opening is performed with a hydrolytic enzyme. The hydrolyitic enzyme, or lipase, can be immobilized or free. In a class of the invention the hydrolytic enzyme is immobilized lipase B from *Candida Antarctica*, lipase from *P. fluorescens*, lipase from *P. cepacia*, lipase A from *C. Antarctica*, lipase from porcine liver or lipase from *P. stutzeri*. In a subclass of the invention, the hydrolytic enzyme is immobilized lipase B from *Candida Antarctica*. Immobilized lipase B from *Candida Antarctica* is commercially available from Novo Nordisk Industries (Bagsveaerd, Denmark) as Novozyme 435.

A variety of oxidizing agents can be used in the deprotection of the alkyl amide. In a class of the invention, the oxidizing agent is DBDMH, iodine, bromine, NBS, NIS or DCDMH. In a subclass of the invention, the oxidizing agent is DBDMH.

The deprotection can take place in the presence of an inorganic acid. In a class of the invention, the inorganic acid has a pKa of less than or equal to 1. In a subclass of the invention, the inorganic acid is hydrochloric acid, triflic acid, sulfuric acid, p-toluenesulfonic acid or trifluoroacetic acid (TFA). In a subclass of the invention, the inorganic acid is trifluoroacetic acid.

The fluorotriflate electrophile of the present invention can be made by fluorinating an epoxide to form a fluoroalcohol, followed by triflating the fluoroalcohol in an organic aprotic solvent to form a fluorotriflate electrophile.

A variety of epoxides can be used in the present invention. In one class of the invention, the epoxide is isobutylene oxide.

Likewise, many fluorinating agents can be used in the present invention. In one class of the invention, the fluorinating agent is Olah's reagent (HF in the form of Pyridine.9HF), HF, LiF or KF. In a subclass of the invention, the fluorinating agent Olah's reagent A variety of triflating agents can be used in the present invention. In one class of the invention, the triflating agent is N-phenyltrifluoromethanesulfonamide or triflate anhydride. In a subclass of the invention, the triflating agent is triflate anhydride.

In one aspect of the invention, the triflation takes place in the presence of a tertiary amine. In one class of the invention, the tertiary amine is triethylamine, Hunig's base, pyridine or Proton Sponge. In a subclass of the invention, the tertiary amine is triethylamine.

Also, the triflation is performed in the presence of an organic aprotic solvent. In one class of the invention, the organic aprotic solvent is MTBE, dichloromethane, dichloroethane, THF, DMF, toluene, heptane, dimethoxyethane, benzene, and hexane, diethyl ether, xylene, or a mixture thereof. In a subclass of the invention the aprotic solvent is MTBE.

Prior to azlactone formation, the substituted imine is hydrolyzed to produce an amine, which upon treatment with an acyl chloride gives the corresponding amide functionality; subsequent saponification of the ester functionality with a strong inorganic base yields the corresponding carboxylic acid.

An acid can be used in the hydrolysis of the imine. In one class of the invention, the acid is hydrochloric acid, citric acid, sulfuric acid, TFA, p-toluenesulfonic acid or triflic acid. In a subclass of the invention, the acid is hydrochloric acid.

A variety of acyl chlorides can be used in the present invention. In one class of the invention, the acyl chloride is 4-pentenoyl chloride, acetyl chloride or benzoylchloride. In a subclass of the invention, the acyl chloride is 4-pentenoyl chloride.

The saponification takes place in the presence of a strong inorganic base. In one class of the invention, the strong inorganic base is sodium hydroxide, lithium hydroxide, potassium hydroxide or potassium carbonate. In a subclass of the invention, the strong inorganic base is sodium hydroxide.

The term "alkyl" as used herein shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc.).

In the schemes and examples below, various reagent symbols and abbreviations have the following meanings:

EDC: 1-Ethyl-3-(3-dimethyllaminopropyl)carbodiimide hydrochloride
DMF: Dimethylformamide
EtOH: Ethanol
HCl: Hydrochloric acid
HF: Hydrogen fluoride
$H_2SO_4$: Sulfuric acid
KOtBu: Potassium t-butoxide
MTBE: t-Butyl methyl ether
$NaHCO_3$: Sodium bicarbonate
NaOH: Sodium hydroxide
$Et_3N$: Triethylamine
RT: Room temperature
TFA: Trifluoroacetic acid
$Tf_2O$: Triflic anhydride
TfOH: trifluoromethanesulfonic acid, triflic acid
THF: Tetrahydrofuran
DBDMH: N,N'-dibromodimethylhydantoin
DCDMH: N,N'-dichlorodimethylhydantoin

EXAMPLE 1

Fluorination

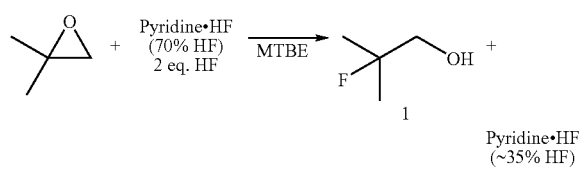

Pyridine.HF (3.97 g) is added to 50 mL MTBE and cooled to −10 to −20 C. Slowly, 5 g of isobutylene oxide is added over 1 hour and let warm to 22-25° C. The mixture is then aged for 16-18 hours. The reaction is quenched by adding 13.87 g aq. $K_2CO_3$ (35% w/w). There is a vigorous evolution of gas with the addition of the aq. $K_2CO_3$. The pH is 8. The layers are separated. The organic layer is dried over 4 A molecular sieves to KF<1000, then filtered.

EXAMPLE 2

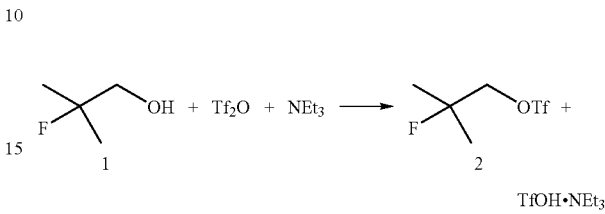

$NEt_3$ (7.85 g) is added to a solution of MTBE (25 mL) and fluoroalcohol 1 (4.7 g), and then cooled to 0-2° C. $Tf_2O$ (17.7 g) is slowly added over 1-2 hours while maintaining the temperature below 15° C. After 15 min, the reactions is assayed for completion by $^1H$ NMR. The solution is quench with 25 mL of 1 N HCl, then the layers are separated. The aqueous layer is extracted with 25 mL MTBE. The organic layers are combined and washed with 12.5 mL sat. $NaHCO_3$. The organic layer is azeotropically dried on the batch concentrator or rotovap, then concentrated to an oil.

EXAMPLE 3

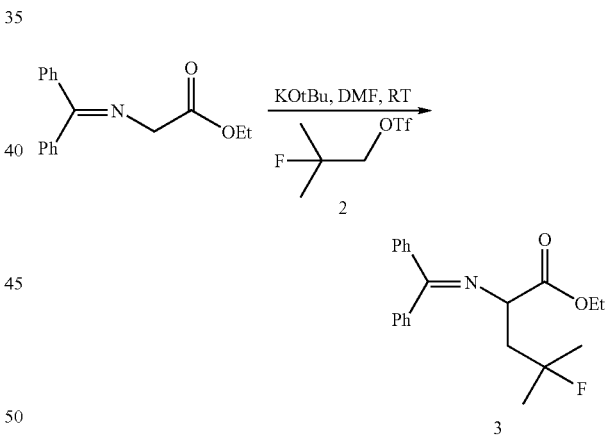

A solution of 4 g diphenylmethylene-glycine ethyl ester in 24 mL DMF is cooled to 0° C. under a $N_2$ atmosphere. A total of 2.0 g potassium t-butoxide is added in portions over 30 minutes at a temperature <10° C. The resulting dark red solution is aged for 1-2 h at 0° C. then cooled to −6° C. The triflate 2 (5.4 g) is added in one portion with the temperature rising to 6° C. over 30 minutes. The reaction is allowed to warm to 20° C. over 2 h and aged overnight. The reaction is charged with 24 mL MTBE, cooled to 2° C., and quenched with 36 mL water with the temperature rising to 20° C. by the end of the addition. The mixture is stirred for 20 minutes and the layers are separated. The MTBE is washed 1×8 L water. The MTBE solution is distilled down to yield 3 an oil.

EXAMPLE 4

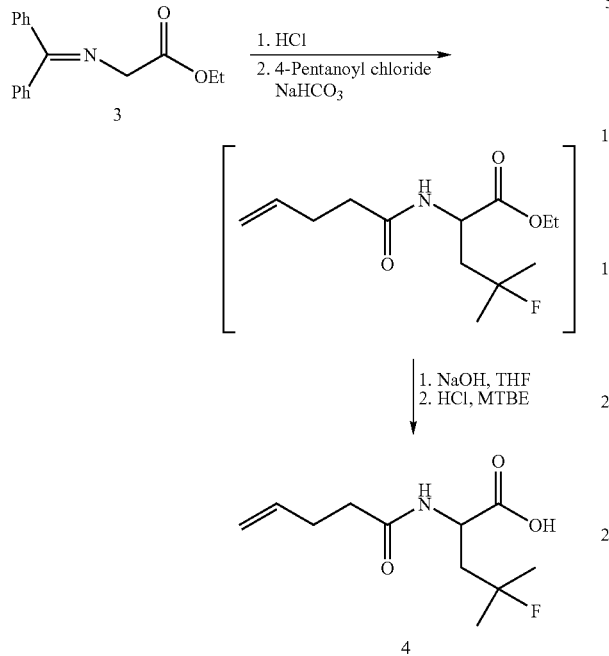

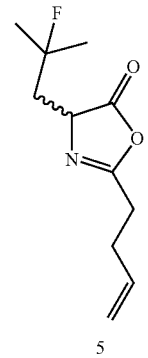

To a solution of imine 3 (7 g) in THF (14 mL) is added aqueous HCl. The reaction is aged 1 h and MTBE (14 mL) is added. The phases are separated and the aqueous phase is diluted with 14 mL THF, and then basified by the addition of solid sodium bicarbonate.

Concurrently, to a solution of pentenoic acid (2.5 mL) in MTBE (14 mL) is added DMF (20 uL) followed by oxalyl chloride (2.15 mL). The chloride is added at such a rate (30-45 min) as to control the gas evolution. The reaction is aged 1 h and then added to the above solution. The addition period is 0.5 h to control gas evolution. The reaction is aged 0.5 h and NaOH (10.3 mL) is added. The reaction is aged overnight. The phases are separated and the aqueous phase is acidified with concentrated HCl (5.5 mL). The aqueous phase is extracted with MTBE (2×20 mL). The combined organic phases are solvent switched into THF and dried to a KF<1000. This generally requires about 40 mL THF. The dried solution of pentamide 4 is stored overnight.

EXAMPLE 5

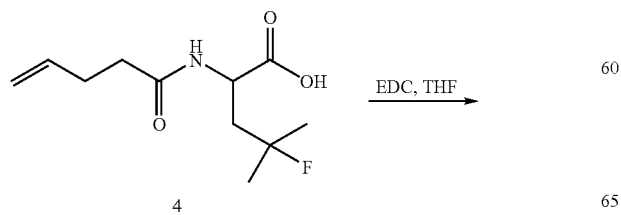

To a solution of pentenamide acid 4 (4.34 g) at 30-35° C. in THF (22 mL) is added EDC (4.32 g). An exotherm of ~5° C. is observed. The urea immediately begins to precipitate from solution as a gummy solid. Heating allows for the mixture to be easily stirred. The reaction is aged 15 min and assayed for completion by $^1$H NMR. Additional EDC can be added if the reaction is not complete. The reaction is then cooled to 30° C. and quenched with water (20 mL), and this is followed by the addition of 20 mL MTBE. The phases are separated and the aqueous phase is extracted 1× MTBE (10 mL). The combined organic phases are washed with water (20 L) and solvent switched into MTBE. The solution is dried to a KF<500 μg/mL by flushing with an additional 40 mL MTBE. The solution of 5 is diluted to 10 mL/g.

EXAMPLE 6

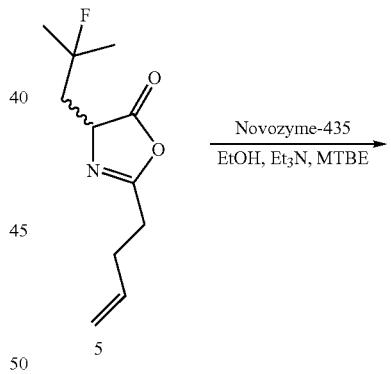

To a solution of oxazolinone 5 (4 g) in MTBE (10 mL/g) at RT is added ethanol (5.6 mL), triethylamine (0.525 mL) and then enzyme (4 g). The reaction is aged until complete by TLC (3-6 h). Upon completion, the reaction is heated to 30-35° C., aged 0.5 h and then filtered. The liquors are cooled to RT and washed with aqueous sodium bicarbonate (20 mL) followed by 1 N HCl. The reaction is azeotropically dried to a KF of 6000 μg and a volume of 20 mL/g.

EXAMPLE 7

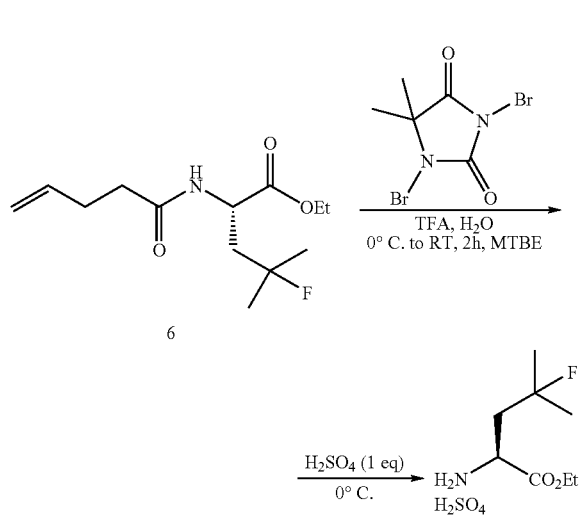

To a visually inspected, 100 mL cylindrical vessel is added a solution of N-Pentenamide ester 6 (4.35 g) in MTBE (20 mL/g). KF of the solution should be less than 4500 ppm. The solution is cooled to 0° C. and treated with trifluoroacetic acid (a 5° C. exotherm is typically observed), followed by solid DBDMH (2.7 g) in portions over 15-20 min (a 10° C. exotherm is usually observed). The resulting reaction mixture is then stirred for 30 min, warmed to RT and aged for 3 hours. The reaction mixture is then transferred in portions into a 100 mL flask and the solvent is removed in vacuo to give a total volume of 7.5 mL/g. The resulting solution is cooled to 0° C., slowly treated with sulfuric acid (0.93 mL) over 15 min (5-10° C. temperature increase is usually observed) and aged for 2 h at 0° C., at which during period of time, the desired product crystallized out. (Seeding might be necessary if no crystals were evident after 15-20 min of stirring). The suspension is then filtered through a filter pot and the wet-cake is washed with a mixture of cold MTBE:iPAc (1:1, 5 mL/g). The collected solid 7 is then dried in vacuo under a stream of $N_2$.

What is claimed is:

1. A process for preparing a compound of formula I:

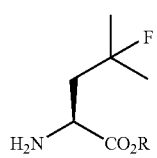

wherein R is hydrogen or $C_{1-6}$ alkyl;

comprising the steps of:
a. Alkylating an imine of formula II. with a fluorotriflate electrophile to form a substitiued imine;

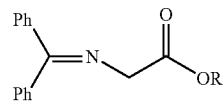

b. Forming an azlactone;
c. Enzymatically opening the azlactone with a hydrolytic enzyme to form an alkyl amide;
d. Deprotecting the alkyl amide with an oxidizing agent to produce the compound of formula I, wherein the hydrolytic enzyme is immobilized lipase B from *C. Antarctica*, lipase from *P. fluorescens*, lipase from *P. cepacia*, lipase A from *C. Antarctica*, lipase from porcine liver or lipase from *P. stutzeri*.

2. The process of claim 1 wherein the alkylation is performed in the presence of a strong base.

3. The process of claim 2 wherein the strong base is potassium t-butoxide, lithium t-butoxide, sodium t-butoxide, lithium diisopropylamide, sodium hydride, n-BuLi, sec-BuLi, t-BuLi, lithium hexamethyldisilazide, sodium hexamethyldisilazide, potassium hexamethyldisilazide or lithium 2,2,6,6-tetramethylpiperidide.

4. The process of claim 3 wherein the strong base is potassium t-butoxide.

5. The process of claim 1 wherein the azlactone formation is performed with a carbonyl activator.

6. The process of claim 5 wherein the carbonyl activator is 1-ethyl-3-(3-dimethylaminopropyl) carbodiimide hydrochloride, N,N'-dicyclohexylcarbodiimide, acetic anhydride, pivaloyl chloride or 1-cyclohexyl-3-(2-morpholinoethyl)carbodiimide metho-p-toluenesulfonate.

7. The process of claim 6 wherein the carbonyl activator is 1-ethyl-3-(3-dimethylaminopropyl) carbodiimide hydrochloride.

8. The process of claim 1 wherein the hydrolytic enzyme is immobilized lipase B from *C. Antarctica*.

9. The process of claim 1 wherein the oxidizing agent is 1,3-dibromo-5,5-dimethylhydantoin, iodine, bromine, N-bromosuccinimide, N-iodosuccinimide or 1,3-dichloro-5,5-dimethylhydantoin.

10. The process of claim 9 wherein the oxidizing agent is 1,3-dibromo-5,5-dimethylhydantoin.

* * * * *